United States Patent [19]

Baldwin et al.

[11] Patent Number: 4,968,713

[45] Date of Patent: Nov. 6, 1990

[54] CERTAIN IMIDAZOLE COMPOUNDS AS TRANSGLUTAMINASE INHIBITORS

[75] Inventors: John J. Baldwin, Gwyneed Valley; David C. Remy, North Wales; David A. Claremon, Audubon, all of Pa.

[73] Assignee: Merck & Co., Inc., Rahway, N.J.

[21] Appl. No.: 386,642

[22] Filed: Jul. 31, 1989

[51] Int. Cl.⁵ .................. A61K 31/415; C07D 233/84
[52] U.S. Cl. .................... 514/398; 548/337
[58] Field of Search ......... 514/398, 822, 88; 548/337

[56] References Cited

U.S. PATENT DOCUMENTS 4,218,476  8/1980  Jöensson et al.
4,265,898  5/1981  Horstmann et al.

FOREIGN PATENT DOCUMENTS 3337181  10/1983  Fed. Rep. of Germany ...... 514/398

OTHER PUBLICATIONS

Kister et al., Can. J. Chem. 57,813 (1979).
Kister et al., Can. J. Chem. 57,822 (1979).

Primary Examiner—Mukund J. Shah
Assistant Examiner—Philip I. Datlow
Attorney, Agent, or Firm—Alice O. Robertson; Charles M. Caruso

[57] ABSTRACT

A method for inhibiting transglutaminase activity, especially Factor XIIIa activity with certain imidazole compounds is described. The imidazole compounds are those selected from
(A) a imidazole having the formula

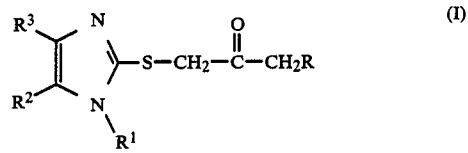

or its acid addition salt, and

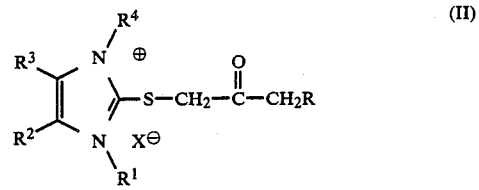

wherein:
R is hydrogen or lower alkyl;
$R^1$ is lower alkyl;
$R^2$ and $R^3$ are independently hydrogen or lower alkyl;
$R^4$ is lower alkyl; and
X is the negative radical of a pharmaceutically acceptable salt.

Also described are compositions suitable for use in inhibiting transglutaminase activity.

19 Claims, No Drawings

CERTAIN IMIDAZOLE COMPOUNDS AS TRANSGLUTAMINASE INHIBITORS

BACKGROUND OF THE INVENTION

Transglutaminases are a family of enzymes which catalyze the amide bond formation of the γ-carboxamide group of peptide glutamine residues with an ε-amino group of peptide lysine residues.

A number of disease states have been associated with transglutaminase activity. Thus, for example, in acne lesions, transglutaminase activity in sebaceous follicles has been reported by DeYoung et. al. in J. Investigative Dermatology, 82, 275 (1984). Also, the cornified cell envelope in acne has been reported to be a result of transglutaminase activity by Dalziel et. al., Br. J. Exp. Pathology, 65, 107–115 (1984).

Another dermatological disease, psoriasis, is reported to be associated with excessive transglutaminase activity by Bernard et. al., British Journal of Dermatology, 114, 279 (1986).

Cataracts also have been reported to be associated with elevated transglutaminase activities.

Factor XIIIa is a plasma transglutaminase which is the activated form of Factor XIII also known as fibrinase or fibrin-stabilizing factor and which catalyzes a number of reactions stabilizing blood clots. It is essential for normal hemostatis and is responsible for the cross-linking of fibrin.

While the activity of this enzyme may be desirable and essential under most circumstances, activity under certain other circumstances can be highly undesirable. Thus, excessive thrombosis, that is, the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is currently looked to in thrombolytic or fibrinolytic therapy. However, a still further reduction in lysis time is necessary to minimize cell injury.

Since Factor XIIIa is an enzyme responsible for the final event in the coagulation of blood, lysis and maintaining the lytic state can be facilitated by the presence of a Factor XIIIa inhibitor. Moreover, the presence of a Factor XIIIa inhibitor would inhibit hard clot formation when thrombosis can be anticipated. Thus, a Factor XIIIa inhibitor is useful in inhibiting hard clot formations, in treating thrombosis when used with a plasminogen activator, a platelet aggregation inhibitor, or an anticoagulant, and in post fibrinolytic therapy in maintaining the lytic state.

STATEMENT OF THE INVENTION

According to the present invention, it has been discovered that certain imidazole compounds, as hereinafter defined, are transglutaminase inhibitors and are therefore useful for treating disease conditions caused by the activity of these enzymes. The imidazoles are particularly useful in inhibiting Factor XIIIa, a plasma transglutaminase, and may be used in thrombolytic or fibrinolytic therapy by administering to a subject in need of such treatment a therapeutically effective amount of the imidazole compound alone, or in admixture with an antithrombotic agent such as a plasminogen activator, a platelet aggregation inhibitor or an anticoagulant.

DETAILED DESCRIPTION OF THE INVENTION

The imidazole compound useful in accordance with this invention, as a transglutaminase inhibitor, particularly as a Factor XIIIa inhibitor, is a compound selected from the group consisting of (A) an imidazole represented by the formula

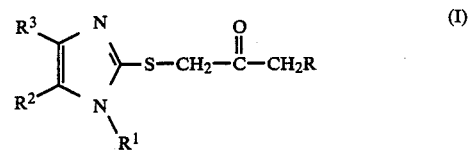

or its acid addition salt, and (B) an imidazolium salt represented by the formula

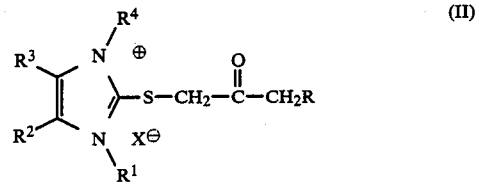

In the above and subsequent formulas,

R is hydrogen or lower alkyl;
$R^1$ is lower alkyl;
$R^2$ and $R^3$ are independently hydrogen or lower alkyl;
$R^4$ is lower alkyl; and
X is a negative radical of a pharmaceutically acceptable salt.

By the expression "lower alkyl" as herein employed is meant from 1 to 6 carbon atoms and is inclusive of straight, branched and cyclic alkyls.

Pharmaceutically acceptable salts suitable as acid addition salts and also as providing the anion of imidazolium salts are those from acids such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, picric and the like, and include acids related to the pharmaceutically acceptable salts listed in Journal of Pharmaceutical Science, 66, 2 (1977) and incorporated herein by reference.

The preferred compounds for use as Factor XIIIa inhibitors are the quaternary imidazolium salts. The imidazoles, on the other hand, are useful additionally as intermediates in the preparation of the preferred quaternary salts.

The compounds useful in the method of the present invention, both those which are acid addition salts of the compounds represented by formula (I) and those quaternary salts represented by formula (II) are usually solids soluble in polar sovents such as water, methanol, ethanol, isopropanol and the like. The imidazoles of formula (I) are soluble in non-polar solvents such as ethyl acetate, methylene chloride, ethylene dichloride, carbon tetrachloride and the like.

Compounds useful as transglutaminase inhibitors, and particularly useful as Factor XIIIa inhibitors adapted to be employed in thrombolytic therapy, may be identified by the Factor XIIIa inhibitor assay hereinafter described. Compounds exhibiting about 50 percent or more inhibition at a concentration of $2 \times 10^{-5}$M in the Factor XIIIa inhibitor assay are generally suitable in thrombolytic therapy. A compound exhibiting such property may be administered to a thrombotic patient susceptible to thrombotic attack either alone or in combination.

Preferably it is employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application No. 028,489). The plasminogen activators may be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi-synthetic proteins or peptides. Established drugs which are platelet aggregation inhibitors include aspirin and dipyridamole. Proteins or polypeptides which are platelet aggregation inhibitors have a certain peptide sequence, most frequently Arg-Gly-Asp. Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Britistatin" and having the amino acid sequence: X-Cys-R-R-R-Arg-Gly-Asp-R-R-R-R-Cys-Y where X is H or an amino acid, Y is OH or an amino acid and each R independently is an amino acid, described and claimed in copending applications Ser. No. 184,649, filed Apr. 22, 1988; Ser. No. 303,757, filed Feb. 1, 1989; and Ser. No. 307,642 filed Feb. 7, 1989, all in the names of P. A. Friedman, et. al., the teachings of which are incorporated by reference.

Additionally, the imidazole compounds may be employed for continued therapy after initial relief from thrombotic attack thereby providing a more complete lysis and minimizing complications from reocclusion. Moreover, the imidazole compounds may be employed in post thrombosis therapy together with anticoagulants such as heparin and coumarin drugs.

The compounds to be employed in the practice of the present invention which are imidazoles may be intermediates in the preparation of those compounds which are imidazolium salts. The latter compounds may be prepared by an alternate procedure in which an imidazole is not an intermediate.

The imidazoles (I) useful in the present invention may be prepared according to the following equation (1): (This method may be referred to as Method A.)

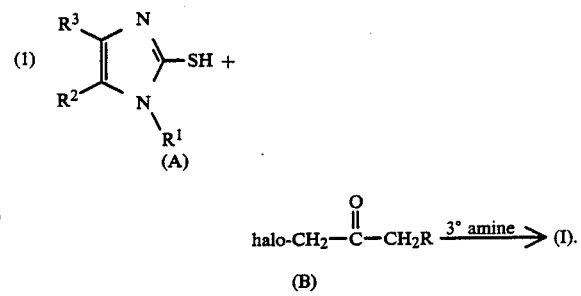

In the preparation of the imidazole of formula (I), the 2-mercaptoimidazole (A) starting material, which may be prepared by known procedures hereinafter detailed, is intimately contacted with and caused to react with an alkanoylmethyl halide (B) in the presence of a tertiary amine (3° amine) in an organic solvent at ambient temperature for time sufficient for reaction to take place with the formation of the desired imidazole of formula (I). After completion of the reaction, the imidazole may be recovered from the reaction mixture by removing the solvent by evaporation and purifying the residue by conventional procedures.

Tertiary amines suitable in the reaction include triethylamine, trimethylamine, pyridine, picolines, collidines, and the like.

Suitable solvents for the reaction include acetone, methyl ethyl ketone, dimethylformamide, dimethyl sulfoxide and the like.

In carrying out the reaction, a solution of the alkanoylmethyl halide is added to a solution of the 2-mercaptoimidazole and tertiary amine and the mixture stirred at room temperature for several hours, conveniently overnight. At the end of this period, the solvent is evaporated and the residue partitioned between water and a water-immiscible organic solvent such as ethyl acetate. The organic solution containing the imidazole is washed and dried, the imidazole recovered from the dried solution as residue, and thereafter, purified, preferably by chromatography on silica gel using methanol/chloroform as eluant.

The imidazole then may be employed in the therapeutic method of the present invention as such or as an acid addition salt, or may be treated as an intermediate and employed in the preparation of the imidazolium salts.

The acid addition salts may be prepared in a conventional manner such as by intimately mixing the imidazole and desired acid, preferably in a minimal amount of polar solvent such as ethanol or by other conventional procedures.

The imidazolium salts may be prepared according to the following equation (2): (This method may be referred to as Method B.)

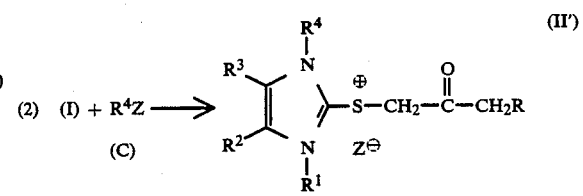

wherein Z is a displaceable group of an active quaternizing agent and within the definition of X. The reaction is carried out by intimately contacting the reactants in a solvent at ambient temperature for time sufficient for the reaction to take place with the formation of an imidazolium salt (II'). The imidazolium salt (II') may be recovered by conventional procedures and purified, if desired, or converted to another imidazolium salt by use of an anion exchange resin.

(2a)    (II') $\xrightarrow{\text{ion exchange}}$ (II)

The quaternizing agent is preferably alkyl trifluoromethylsulfonate or other active agent. Alkyl chlorides tend to be inert and alkyl iodides, especially methyl iodide, has been found to be unstable. Thus, the halide salts and many other salts are preferably prepared from the trifluoromethylsulfonate.

The reaction may be carried out for from as little as about two hours to a week or so, depending on the particular reactants.

In carrying out the reaction, methyl trifluoromethylsulfonate is added to a solution of the appropriate imidazole (I) in a non-polar organic solvent such as methylene chloride and the resulting mixture stirred at ambient temperature for time sufficient for substantial completion of the reaction. At the end of this period, the solvent is vaporized and the residue crystallized to obtain the trifluoromethylsulfonate salt or is converted into a halide by ion-exchange chromatography, using methanol/water as solvent. The resulting imidazolium salt is recovered from the eluate and purified, if desired, by conventional procedures.

The imidazolium compound represented by formula (II) may be prepared by an alternate procedure in which a 1,3-disubstituted-imidazoline-2-thione is caused to react according to the following equation:

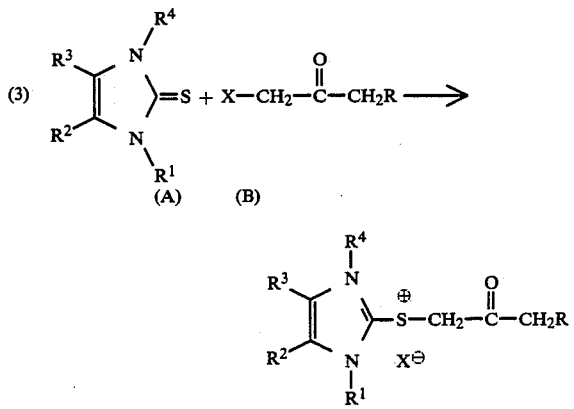

This method is especially convenient when X is halogen.

The thione starting material may be prepared as hereinafter described or by any alternative procedure known to the skilled in the art. It may be prepared as the first step and RCH$_2$COCH$_2$X added to the reaction mixture.

In the reaction between the thione and RCH$_2$COCH$_2$X, about equimolar amounts of the reactants are employed and the reaction is carried out in solution. Solvents suitable for carrying out the reaction are acetone, methyl ethyl ketone and the like. The reaction may be carried out between about 20° to about 50° C. over a period of from about 4 to about 24 hours. Conveniently, the reaction may be carried out by stirring overnight. The reaction may be catalyzed by the addition of a small crystal of sodium iodide.

In carrying out the reaction, the alkanoylmethyl halide (B) is added to a solution of the imidazoline-2-thione (A) and the resulting mixture stirred together for time sufficient to complete the reaction with the formation of the desired imidazolium salt which precipitates in the reaction mixture. The imidazolium salt product may be recovered and purified by conventional procedures.

The imidazolium salts in which X$^-$ is halide may be converted to salts in which X$^-$ is trifluoromethylsulfonate or another anion by charging an ion-exchange column with the sodium salt of trifluoromethylsulfonate or other desired anion in a conventional manner. Thereafter, the imidazolium halide is charged on the column in a solvent such as methanol and the desired imidazolium salt recovered from the eluate by vaporizing off the solvent.

The usefulness of the imidazole compounds for enchancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}$C-putrescine into casein catalyzed by Factor XIIIa. The assay is carried out employing the procedure described in Methods in Enzymology, Vol. 45, Ch 15., pages 177–191 (1976) and using Factor XIII (F XIII) isolated from human plasma. The procedure is summarized briefly and schematically illustrated as follows:

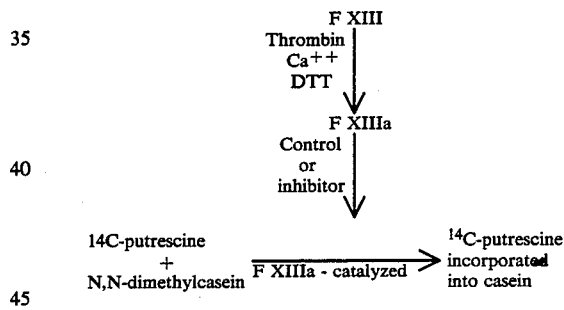

Factor XIII assay mixtures are prepared by adding stepwise, appropriately prepared solutions of thrombin and dithiothreitol (DTT) to a mixture comprising Factor XIII at 140 μg/mL in glycerol/water and tris(hydroxymethyl)aminomethane hydrochloride (Tris.HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}$C-putrescine and N,N-dimethylcasein.

The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}$C-putrescine and after drying is counted for $^{14}$C-putrescine incorporated to casein from which percent activity and/or inhibition can be calculated.

The results with imidazoles and imidazolium compounds may be seen in the following table:

| Compound | | | | | Anion or Salt | Percent inhibition (Molar concn) |
|---|---|---|---|---|---|---|
| R | $R^1$ | $R^2$ | $R^3$ | $R^4$ | | |
| H | $CH_3$ | H | H | — | — | 40% @ 0.15 μM |
| H | $CH_3$ | $CH_3$ | $CH_3$ | — | HCl | 76% @ 3.7 μM |
| H | $CH_3$ | $CH_3$ | H | — | HCl | 47% @ 2 μM |
| H | $CH_3$ | $CH_3$ | $C_3H_7$ | — | HCl | 46% @ 4 μM |
| H | $CH_3$ | $CH_3$ | $CH_3$ | $CH_3$ | $Cl^-$ | 95% @ 80 nM |
| $CH_3$ | $CH_3$ | $CH_3$ | $CH_3$ | $CH_3$ | $CF_3SO_3^-$ | 93% @ 100 nM |
| H | $CH_3$ | $CH_3$ | H | $CH_3$ | $CF_3SO_3^-$ | 90% @ 100 nM |
| H | $CH_3$ | $C_3H_7$ | $C_3H_7$ | $CH_3$ | $CF_3SO_3^-$ | 86% @ 100 nM |
| H | $CH_3$ | H | H | $CH_3$ | $I^-$ | 44% @ 110 nM |
| H | $CH_3$ | H | H | $CH_3$ | $Cl^-$ | 67% @ 313 nM |
| H | $CH_3$ | $CH_3$ | $CH_3$ | $CH_3$ | $CF_3SO_3^-$ | 95% @ 80 nM |
| H | $CH_3$ | iPr | iPr | $CH_3$ | $CF_3SO_3^-$ | 44% @ 1.0 μM |

Factor XIIIa inhibitors showing at least 50 percent activity at $2\times10^{-5}$M in the Factor XIIIa assay show positive ability to lyse clots and are considered to be useful in inhibiting hard clot formation or especially in supplementing fibrinolysis by plasminogen activator.

The process of the present invention for inhibiting hard clot formation and thereby facilitating clot lysis and maintaining the lytic state comprises administering a therapeutic dose of an imidazole compound in a composition comprising the same. In general, the dose may be that sufficient to provide between about 1.4 milligrams per kilogram of body weight per day to about 140 milligrams/kilogram/day while considering patient's health, weight, age and other factors which influence drug response. The drug may be administered per os or by injection and if by injection, either by a single injection, multiple injections or continuous infusion.

In the preferred process of the present invention, the imidazole compound is administered with a plasminogen activator in a combination therapy. When combination therapy is employed, it is preferable to administer the Factor XIIIa inhibitor imidazole compound first in a single bolus and thereafter to administer the plasminogen activator by continuous infusion. However, both may be administered simultaneously as a continuous infusate. Under certain circumstances it may be desirable to administer the imidazole compound subsequent to the administeration of the plasminogen activator. It is intended that the method of the present invention embrace concurrent administration as well as sequential administration, in any order.

When the Factor XIIIa inhibitor imidazole compound and plasminogen activator are employed in a combination therapy, it is most desirable to use the plasminogen activator in the dose range of about 500 to 10,000 I.U./kg/minute for from about 30 to 180 minutes and the imidazole compound in the range of 1 μg–100 μg/kg/minute for a day (1440 minutes).

When the imidazole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose of 25–325 mg twice a day. When the platelet aggregation inhibitor compound is dipyridamole, the dipyridamole may be employed at a dose of 25–100 mg four times a day. When the platelet aggregation inhibitor is a semi-synthetic peptide such as "Echistatin" or "Bitistatin", the peptide may be administered in a dose range of 0.1 to 1 nanomole/kg/min. for from 30 to 180 minutes. In each case, the imidazole compound may be employed in the range of 1–100 μg/kg min. for a day. The administration may be carried out simultaneously or sequentially in any order as in the procedure for administration with plasminogen activators.

When the imidazole compound is to be used with heparin, heparin may be administered at dose of 4000 to 8000 units per 4 hours and the imidazole compound in the range of 1 μg–100 μg/kg/minute for day. When it is to be used with coumarin drugs these drugs are administered orally at doses of 10 to 15 μg/kg/day and the imidazole compound administered by infusion at a rate of 1 μg–100 μg/kg/minute for a day.

Compositions to be employed in the practice of the present invention whether parenteral, oral or suppository compositions comprises an imidazole compound in a pharmaceutically acceptable carrier.

Parenteral compositions comprises the imidazole compound in sterile physiologically acceptable media such as physiological saline. Such compositions may also contain other ingredients for purposes such as for aiding solubility or for preservation or the like, said ingredients being those acceptable for intravenous administration. The compositions may be prepared as concentrate compositions and lyophilized and then diluted the appropriate treating composition immediately prior to administration. A therapeutic composition as a unit dose form may contain from 100 mg to 10 grams of imidazole compound. Compositions suitable in the preferred practice of the present invention of co-administering plasminogen activator and Factor XIIa inhibitor compound may contain (a) about 58 million I.U. of tPA or 1.5 million I.U. of streptokinase as plasminogen activator and (b) from 100 mg to 10 grams of the imidazole compound.

Oral compositions also may be prepared with the active ingredient in admixture with a pharmaceutically acceptable carrier. Suitable carriers for liquid compositions include water, glycols, oils, alchols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

Suppository compositions may be prepared with ointments, jellies, carbowax, polyethylene sorbitan monostearate, polyethylene glycol, cocoa butter, and other conventional carriers.

The preparation of the imidazole compounds suitable for inhibiting transglutaminase enzymes, particularly Factor XIIIa, and compositions suitable for carrying out the process of the present invention are illustrated by the following examples but are not to be construed as limiting.

EXAMPLE 1

A. 1,4,5-Trimethyl-2[(2-oxopropyl)thio]imidazole

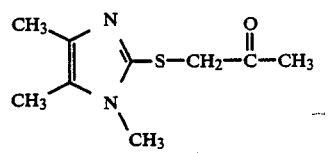

Chloroacetone, 2.55 grams (0.28 mol) in 250 mL of acetone, was added to a solution of 3.55 g (0.025 mol) of 1,4,5-trimethyl-2-mercaptoimidazole and 3.15 g (0.031 mol) of triethylamine in 250 mL of acetone and the resulting mixture stirred at room temperature for 16 hours. At the end of this period the acetone was removed by evaporation and the residue was partitioned between ethyl acetate and water. The ethyl acetate solution was washed successively with water and brine, and then dried over magnesium sulfate. After drying, the solvent was evaporated from the filtered dry solution to obtain 3.39 grams of 1,4,5-trimethyl-2[(2-oxopropyl)thio]imidazole. The latter was purified by flash chromatography on silica gel using 1 percent methanol in chloroform as an eluant to obtain 3.0 grams of purified 1,4,5-trimethyl-2[(2-oxopropyl)thio]imidazole.

B.
1,3,4,5-Tetramethyl-2[(2-oxopropyl)thio]imidazolium chloride (and trifluoromethylsulfonate)

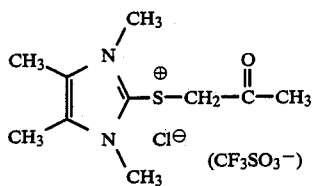

To a solution of 3.0 grams (0.015 mol) of the above prepared imidazole in 20 mL of methylene chloride was added 2.48 g (0.015 mol) of methyl trifluoromethylsulfonate and the solution was stirred overnight at room temperature. The solvent was then evaporated to obtain 1,3,4,5-tetramethyl-2[(2-oxopropyl)thio]imidazolium trifluoromethylsulfonate as residue.

The trifluoromethylsulfonate salt was converted to the corresponding chloride salt by ion-exchange chromatography using Dowex-1 (Cl⁻) absorbent and 20 percent methanol in water solvent. After evaporating the solvent from the eluate, the remaining residue was crystallized from isopropyl alcohol-hexane to obtain 1,3,4,5-tetramethyl-2[(2-oxopropyl)thio]imidazolium chloride, m.p. 172°-175° C.

Anal. Calcd for $C_{10}H_{17}ClN_2OS$: C, 48.28; H, 6.89; N, 11.26; Found: C, 48.33; H, 7.02; N, 10.82.

EXAMPLE 2

In reactions carried out in a manner similar to that described in Example 1, the following compounds were prepared:

1,5-Dimethyl-2[(2-oxopropyl)thio]imidazole
1,3,5-Trimethyl-2[(2-oxopropyl)thio]imidazolium trifluoromethylsulfonate, m.p. 65°-67° C.

Anal. Calcd for $C_{10}H_{15}N_2F_3S_2O_4$: C, 34.48; H, 4.34; N, 8.04; Found: C, 34.40; H, 4.31; N, 8.05.

1-Methyl-4,5-di(n-propyl)-2-[(2-oxopropyl)thio]imidazole.

1,3-Dimethyl-4,5-di(n-propyl)-2-[(2-oxopropyl)thio]imidazolium trifluoromethylsulfonate, m.p. 77.5°-79.5° C.

Anal. Calcd for $C_{15}H_{25}N_2F_3S_2O_4$: C, 43.05; H, 6.02; N, 6.69; Found: C, 43.02; H, 6.18; N, 6.78.

EXAMPLE 3

1,3,4,5-Tetramethyl-2-[(2-oxopropyl)thio]imidazolium chloride

Chloroacetone, 5.55 g (0.06 mol), was added to a solution of 9.38 g (0.06 mol) of 1,3,4,5-tetramethyl-imidazoline-2-thione in 180 mL of acetone and to which a small crystal of sodium iodide had been added. The resulting mixture was stirred overnight whereupon 1,3,4,5-tetramethyl-2-[(2-oxopropyl)thio]imidazolium chloride was found to have precipitated in the reaction mixture. The precipitate was recovered by filtration and recrystallized from isopropyl alcohol-hexane to obtain a purified imidazolium chloride salt, m.p. 172°-175° C.

Anal. Calcd. for $C_{10}H_{17}ClN_2OS$: Calcd: C, 48.28; H, 6.89; N, 11.26; Found: C, 48.25; H, 6.85; N, 11.19.

EXAMPLE 4

In operations carried out in a manner similar to that described in Example 3, the following imidazolium salts may be prepared:

1,3,4,5-Tetraethyl-2-[(2-oxopropyl)thio]imidazolium chloride by the reaction of 1,3,4,5-tetraethylimidazoline-2-thione and chloroacetone.

4,5-Diethyl-1,3-diisopropyl-2-[(2-oxobutyl)thio]imidazolium chloride by the reaction of 4,5-diethyl-1,3-diisopropyl-imidazoline-2-thione and 1-chloro-2-butanone.

5-Pentyl-1,3-dimethyl-2-[(2-oxopropyl)thio]imidazolium bromide by the reaction of 5-pentyl-1,3-dimethyl-imidazoline-2-thione and 1-bromoacetone.

1,3,4,5-Tetramethyl-2-[(2-oxohexyl)thio]imidazolium chloride by the reaction of 1,3,4,5-tetramethyl-)imidazoline-2-thione and 1-chloro-2-hexanone.

4,5-Dicyclohexyl-1,3-dimethyl-2-[(2-oxobutyl)thio]imidazolium chloride by the reaction of 4,5-dicyclohexyl-1,3-dimethyl-imidazoline-2-thione and 1-chloro-2-butanone.

1,3,4,5-Tetramethyl-2-[(3-cyclohexyl-2-oxopropyl)thio]imidazolium chloride by the reaction of 1,3,4,5-tetramethyl)imidazoline-2-thione and 1-chloro-3-cyclohexylpropanone.

EXAMPLE 5

Parenteral Composition

One liter of a parenteral composition comprising one of the foregoing compounds may be prepared from the following formulation:

|  | Grams |
| --- | --- |
| Imidazolium Salt | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP | q.s. to 1 liter |

The parabens, sodium chloride and carboxymethyl-cellulose are dissolved in one-half the total volume of water by heating to 95° C. to obtain a solution which is then filtered and autoclaved. The polysorbate is dissolved in one-third of the total volume of water, and the resulting solution also is filtered and autoclaved. The sterile active ingredient is added to the second solution and the mixture passed through a sterile colloid mill to obtain a suspension of active ingredient. The first solution is added to the suspension with stirring, then U.S.P. water is added to 1 liter. Sterile vials are filled with the suspension while stirring.

EXAMPLE 6

Oral Composition 5000 compressed tablets, each containing as active ingredient 100 milligrams of one of the foregoing compounds, may be prepared from the following formulation:

|  | Grams |
|---|---|
| Imidazolium Salt | 500 |
| Starch | 700 |
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

Preparation of the Starting Materials

A. 2-Mercaptoimidazole

The 2-mercaptoimidazoles may be obtained by a reaction between an appropriate acyloin and mono-substituted urea according to the following equation:

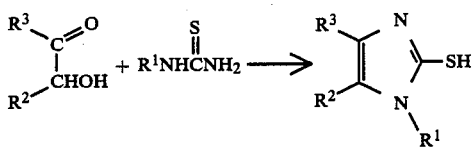

The reaction may be carried out by fusing the reactants or by refluxing the components in hexanol-1 as more fully described by Nuhn, P. et. al., J. fur praktische Chemie, 312, 90 (1970) for the fusion method and by Kjellin, G. et. al., Acta Chemica Scandinavica, 23, 2879 (1969) for the method where the α-hydroxyketones and N-alkylthioureas are refluxed in 1-hexanol with a water separator. The teachings of the foregoing articles on the preparation of the starting 2-mercaptoimidazoles are incorporated by reference.

B. 1,3-Disubstituted-imidazoline-2-thione 1,3-Disubstituted-imidazoline-2-thione may be obtained by the reaction between an α-hydroxyketone and di-substituted thiourea according to the equation

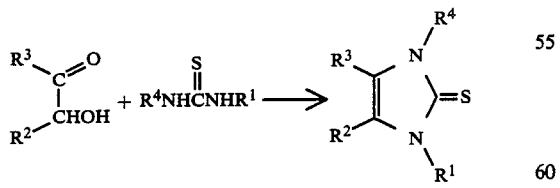

The reactants may be intimately contacted in the manner above described for the preparation of the mercaptoimidazoles.

What is claimed is:

1. A method for inhibiting the action of Factor XIIIa transglutaminase enzyme in thrombolytic or fibrinolytic therapy which comprises administering to a subject in need of such treatment, a therapeutically effective enzyme inhibitory amount of an imidazole compound in a composition comprising said imidazole compound in a pharmaceutically acceptable carrier, wherein said imidazole compound is selected from the group consisting of (A) an imidazole having the formula

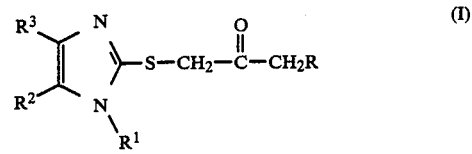

or its acid addition salt, and (B) an imidazolium salt having the formula

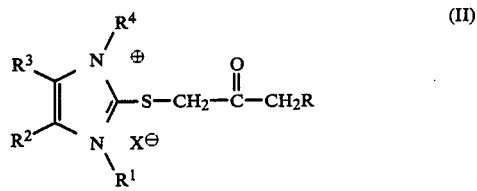

wherein:
R is hydrogen or lower alkyl;
$R^1$ is lower alkyl;
$R^2$ and $R^3$ are independently hydrogen or lower alkyl;
$R^4$ is lower alkyl; and
X is the negative radical of a pharmaceutically acceptable salt in admixture with a pharmaceutically acceptable carrier.

2. A method for inhibiting hard clot formation or facilitating clot lysis in thrombotic patients which comprises administering a therapeutically effective amount of a composition comprising an imidazole compound selected from the group consisting of (A) an imidazole represented by the formula

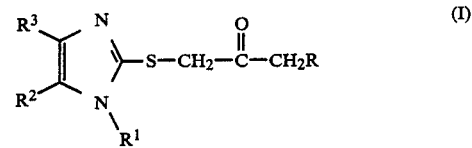

or its acid addition salt, and (B) an imidazolium salt represented by the formula

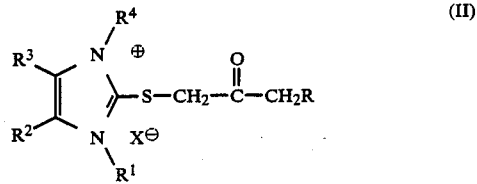

wherein:
R is hydrogen or lower alkyl;
$R^1$ is lower alkyl;
$R^2$ and $R^3$ are independently hydrogen or lower alkyl;
$R^4$ is lower alkyl; and X is a negative radical of a pharmaceutically acceptable salt.

3. A method according to claim 2 wherein the imidazole compound is an imidazolium salt.

4. A method according to claim 3 wherein the imidazolium salt is 1,3,4,5-tetramethyl-2-[(2-oxopropyl)thio]imidazolium chloride.

5. A method according to claim 3 wherein the imidazolium salt is 1,3,4,5-tetramethyl-2-[(2-oxopropyl)thio]imidazolium trifluoromethanesulfonate.

6. A method according to claim 3 wherein the imidazolium salt is 1,3,4,5-tetramethyl-2-[(2-oxobutyl)-thio]imidazolium trifluoromethanesulfonate.

7. A method according to claim 3 wherein the imidazolium salt is 1,3,5-trimethyl-2-[(2-oxopropyl)thio]imidazolium trifluoromethanesulfonate.

8. A method according to claim 3 wherein the imidazolium salt is 1,3-dimethyl-4,5-di-(n-propyl)-2-[(2-oxopropyl)thio]imidazolium trifluoromethanesulfonate.

9. A method according to claim 3 wherein the imidazolium salt is 1,3-dimethyl-2-[(2-oxopropyl)thio]imidazolium chloride.

10. A method according to claim 3 wherein from 1 μg–100 μg/kg/min for a day (1440 minutes) of the imidazole compound is administered.

11. A method according to claim 3 wherein an antithrombotic agent is also administered.

12. A method according to claim 11 wherein the antithrombotic agent is a plasminogen activator.

13. A method according to claim 11 wherein the antithrombotic agent is a platelet aggregation inhibitor.

14. A method according to claim 11 wherein the antithrombotic agent is an anticoagulant.

15. A composition adaptable for use thrombolytic therapy comprising a Factor XIIIa inhibitor imidazole compound in a pharmaceutically acceptable carrier wherein said imidazole compound is one having the formula (A) an imidazole having the formula

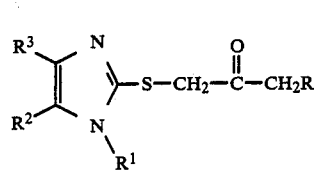

(I)

or its acid addition salt, or (B) an imidazolium salt having the formula

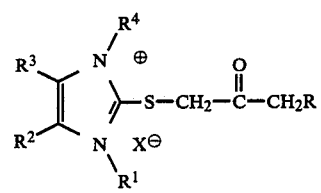

(II)

wherein:
R is hydrogen or lower alkyl;
$R^1$ is lower alkyl;
$R^2$ and $R^3$ are independently hydrogen or lower alkyl;
$R^4$ is lower alkyl; and
X is a negative radical of a pharmaceutically acceptable salt.

16. A composition according to claim 15 containing 100 mg to 10 grams of the imidazole compound.

17. A composition suitable for thrombolytic therapy in unit dosage form comprising (1) about 58 million I.U. of tissue plasminogen activator (tPA) or about 1.5 million I.U. of streptokinase as plasminogen activator and (2) from 100 mg to 10 grams of an imidazole compound according to claim 1, in admixture with a pharmaceutically acceptable carrier.

18. A composition according to claim 17 in which the plasminogen activator is tissue plasminogen activator (tPA).

19. A composition according to claim 17 in which the plasminogen activator is streptokinase.

* * * * *